United States Patent [19]

Morioka et al.

[11] Patent Number: 5,801,016
[45] Date of Patent: Sep. 1, 1998

[54] DNA FRAGMENT, RECOMBINANT VECTOR CONTAINING THE SAME AND METHOD FOR EXPRESSING FOREIGN GENES USING THE SAME

[75] Inventors: Shinji Morioka; Jun Ueki, both of Iwata-gun, Japan

[73] Assignee: Japan Tobacco Inc., Tokyo, Japan

[21] Appl. No.: 750,007

[22] PCT Filed: Mar. 28, 1996

[86] PCT No.: PCT/JP96/00812

§ 371 Date: Nov. 27, 1996

§ 102(e) Date: Nov. 27, 1996

[87] PCT Pub. No.: WO96/30510

PCT Pub. Date: Oct. 3, 1996

[30] Foreign Application Priority Data

Mar. 29, 1995 [JP] Japan .................................. 7-096126

[51] Int. Cl.$^6$ .................................................. C12P 21/02
[52] U.S. Cl. ..................... 435/69.1; 435/320.1; 536/24.1
[58] Field of Search ..................... 435/69.1, 320.1; 536/24.1

[56] References Cited

FOREIGN PATENT DOCUMENTS 3-103182  4/1991  Japan .

OTHER PUBLICATIONS

Tanaka et al, Nucleic Acids Research, vol. 18, No. 23, pp. 6767–6770 (1990).

*Primary Examiner*—James Ketter
*Attorney, Agent, or Firm*—Birch, Stewart, Kolasch & Birch, LLP

[57] ABSTRACT

Disclosed is a novel DNA which can promote expression of foreign genes and which has a nucleotide sequence different from those of known DNAs that promote expression of foreign genes. The present invention provides an isolated DNA fragment having a nucleotide sequence shown in SEQ ID NO. 1 in Sequence Listing or having a nucleotide sequence which is the same as the nucleotide sequence shown in SEQ ID NO. 1 in Sequence Listing except that one or a plurality of nucleotides are added, inserted, deleted or substituted, the latter nucleotide sequence having a function to promote expression of a gene downstream thereof.

9 Claims, 1 Drawing Sheet

FIG.1

DNA FRAGMENT, RECOMBINANT VECTOR CONTAINING THE SAME AND METHOD FOR EXPRESSING FOREIGN GENES USING THE SAME

TECHNICAL FIELD

The present invention relates to a novel DNA fragment having function to promote expression of genes, a vector containing the same and a method for expressing foreign genes using the same.

BACKGROUND ART

Promotion of expression of foreign genes is one of the most important techniques in applying genetic engineering processes to plants. One of the methods therefor is utilization of a DNA having a nucleotide sequence which promotes expression of a gene.

Known nucleotide sequences which promote expression of foreign genes include the intron of the catalase gene of castor bean (Japanese Laid-open Patent Application (Kokai) No. 3-103182; Tanaka et al., Nucleic Acids Res. 18, 6767–6770 (1990)). However, since there are wide varieties of plants to be manipulated and since promotion of expression of genes is required in each of the desired growth stages or tissues of organs, it is desired that wide varieties of DNAs which promote expression of genes can be utilized.

DISCLOSURE OF THE INVENTION

Accordingly, an object of the present invention is to provide a novel DNA, which can promote expression of foreign genes and which has a nucleotide sequence different from those of known DNAs that promote expression of foreign genes.

The present inventors intensively studied to discover introns of rice phospholipase D (hereinafter also referred to as "PLD") gene by comparing a rice cDNA and a rice genomic DNA, and discovered that one of the introns has a function to prominently promote expression of the gene downstream thereof, thereby completing the present invention.

That is, the present invention provides an isolated DNA fragment having a nucleotide sequence shown in SEQ ID NO. 1 in Sequence Listing or having a nucleotide sequence which is the same as the nucleotide sequence shown in SEQ ID NO. 1 in Sequence Listing except that one or a plurality of nucleotides are added, inserted, deleted or substituted, the latter nucleotide sequence having a function to promote expression of a gene downstream thereof. The present invention also provides a recombinant vector comprising the above-mentioned DNA fragment according to the present invention and a foreign gene to be expressed, which is operably linked to the DNA fragment at a downstream region of the DNA fragment. The present invention further provides a method for expressing a foreign gene comprising introducing the recombinant vector according to the present invention into host cells and expressing the foreign gene.

As experimentally confirmed in the Example described below, the DNA fragment according to the present invention largely promotes expression of the gene downstream of the DNA fragment. Therefore, it is expected that the present invention will largely contribute to expression of foreign genes by genetic engineering processes.

BEST MODE FOR CARRING OUT THE INVENTION

As mentioned above, the DNA fragment according to the present invention has a nucleotide sequence shown in SEQ ID NO. 1 in the Sequence Listing. As will be described in detail in the Example below, introns located upstream of rice PLD gene were identified by comparing the nucleotide sequence of the cDNA of rice PLD gene and that of the rice genomic DNA. A fragment containing one of these intron sequences having a size of 173 bp located at the 5'-flanking region was prepared by PCR and the DNA fragment was inserted into an upstream site of a reporter gene of an expression vector containing the reporter gene. By checking the expression activity of the reporter gene, it was confirmed that the DNA fragment has a function to promote expression of the gene downstream thereof. The nucleotide sequence of the DNA fragment according to the present invention corresponds to 1661nt to 1843nt of the nucleotide sequence of the rice genomic PLD gene, which nucleotide sequence is shown in SEQ ID NO: 4 of the Sequence Listing.

The nucleotide sequence of the above-mentioned intron sequence having a size of 173 bp, which is located upstream of the rice PLD gene, is shown in SEQ ID NO: 7 in the Sequence Listing. Needless to say, the sequence shown in SEQ ID NO: 7 also has a function to promote expression of the gene downstream thereof. The nucleotide sequence shown in SEQ ID NO: 7 corresponds to 1666nt to 1838nt of the nucleotide sequence of the rice genomic PLD gene, which is shown in SEQ ID NO: 4 in the Sequence Listing.

Since the DNA fragment according to the present invention is an intron existing upstream of the rice PLD gene, and since its nucleotide sequence was determined according to the present invention, the DNA fragment may easily be prepared by PCR using the rice genomic DNA as a template. PCR is a conventional technique widely used in the field of genetic engineering and a kit therefor is commercially available, so that those skilled in the art can easily perform the PCR. One concrete example thereof is described in detail in the Example below.

It is well-known in the art that there are cases wherein the physiological activity of a physiologically active DNA sequence is retained even if the nucleotide sequence of the DNA is modified to a small extent, that is, even if one or more nucleotides are added, inserted, deleted or substituted. Therefore, DNA fragments having the same nucleotide sequence as shown in SEQ ID NO. 1 except that the DNA fragments have such modifications, which have the function to promote expression of the gene downstream thereof, are included within the scope of the present invention. That is, the DNA fragments having the same nucleotide sequence as shown in SEQ ID NO. 1 except that one or more nucleotides are added, deleted or substituted, which have the function to promote expression of the gene downstream thereof, are included within the scope of the present invention. Particularly, in the nucleotide sequence shown in SEQ ID NO. 1, the 5 nucleotides at the 5'-end and the 5 nucleotides at the 3'-end are the nucleotides in the exon regions, so that it is thought that the nucleotide sequences which do not have these regions also have the function to promote gene expression. Thus, these DNA fragments are within the scope of the present invention.

Modification of DNA which brings about addition, deletion or substitution of the amino acid sequence encoded thereby can be attained by the site-specific mutagenesis which is well-known in the art (e.g., Nucleic Acid Research, Vol. 10, No. 20, p6487–6500, 1982). In the present specification, "one or a plurality of nucleotides" means the number of nucleotides which can be added, deleted or substituted by the site-specific mutagenesis.

Site-specific mutagenesis may be carried out by, for example, using a synthetic oligonucleotide primer complementary to a single-stranded phage DNA except that the desired mutation as follows. That is, using the above-mentioned synthetic oligonucleotide as a primer, a complementary chain is produced by a phage, and host bacterial cells are transformed with the obtained double-stranded DNA. The culture of the transformed bacterial cells is plated on agar and plaques are formed from a single cell containing the phage. Theoretically, 50% of the new colonies contain the phage having a single-stranded chain carrying the mutation and remaining 50% of the colonies contain the phage having the original sequence. The obtained plaques are then subjected to hybridization with a kinase-treated synthetic probe at a temperature at which the probe is hybridized with the DNA having exactly the same sequence as the DNA having the desired mutation but not with the original DNA sequence that is not completely complementary with the probe. Then the plaques in which the hybridization was observed are picked up, cultured and the DNA is collected.

In addition to the above-mentioned site-specific mutagenesis, the methods for substituting, deleting or adding one or more amino acids without losing the function include a method in which the gene is treated with a mutagen and a method in which the gene is selectively cleaved, a selected nucleotide is removed, added or substituted and then the gene is ligated.

The DNA fragment according to the present invention has a function to promote expression of the gene downstream thereof. Therefore, by inserting the DNA fragment according to the present invention into the transcriptional region of a desired foreign gene to be expressed, preferably into the 5'-end region of the transcriptional region, expression of the foreign gene is promoted. The method for expressing a foreign gene has already been established in the field of genetic engineering. That is, by inserting the desired foreign gene into a cloning site of an expression vector, introducing the resulting vector into host cells and expressing it, the foreign gene may be expressed. According to the method of the present invention, the DNA fragment according to the present invention is inserted at a site upstream of the foreign gene in a manner such that the DNA fragment is operably linked to the foreign gene, and the foreign gene is expressed. The term that the DNA fragment according to the present invention is "operably linked" to the foreign gene means that expression of the foreign gene is detectably increased by inserting the DNA fragment according to the present invention when compared with the case wherein the DNA fragment according to the present invention is not inserted. The DNA according to the present invention may be inserted into the site immediately upstream of the foreign gene. Alternatively, another sequence may be located between the DNA according to the present invention and the foreign gene. Although the size of this intervening sequence is not restricted, it usually has a size of 0–1000 bp. A promoter sequence is located upstream of the DNA fragment according to the present invention. The DNA fragment according to the present invention may be inserted into the site immediately downstream of the promoter, or another sequence may be located between the promoter and the DNA according to the present invention. Although the size of this intervening sequence is not restricted, it is usually 0–1000 bp. In summary, all recombinant vectors with which the expression of the foreign gene is detectably increased by inserting the DNA fragment according to the present invention when compared with the case wherein the DNA fragment is not inserted, are within the scope of the present invention.

Since the nucleotide sequence of the cloning site of an expression vector is known, the DNA fragment according to the present invention may easily be inserted into the vector.

Wide varieties of such an expression vector are well-known in the art and are commercially available. These expression vectors contain at least a replication origin for replication in the host cells, a promoter, a cloning site giving a restriction site for inserting the foreign gene, and a selection marker such as drug resistance, and usually contain a terminator which stably terminates transcription, and an SD sequence when the host is a bacterium. In the method of the present invention, any of these known expression vectors may be employed.

Example

The present invention will now be described in more detail by way of examples thereof. However, the present invention is not restricted to the examples.

1. Purification of PLD of Rice Bran

For purification, a reference (Takano et al., Journal of Japan Food Industry Association, 34, 8–13 (1987) was referred. The enzyme activity was measured by employing phosphatidylcholine as a substrate and quantifying the choline generated by the enzyme reaction (Imamura et al., J. Biochem. 83, 677–680 (1978)). It should be noted, however, the enzyme reaction was stopped by heat treatment at 95° C. for 5 minutes.

That is, to 100 g of bran of rice (Oryza sativa), variety "KOSHIHIKARI", one liter of hexane was added and the mixture was stirred for a whole day and night, thereby defatting the rice bran. To the resultant, 10 g of Polycral AT (trademark, polyvinylpyrrolidone, commercially available from GAF Chemical) and 500 ml of 10 mM Tris-HCl buffer (pH7) containing 1 mM $CaCl_2$ and 5 mM 2-mercaptoethanol were added, and the resulting mixture was stirred for 1 hour to extract the enzyme. The extract was filtered through an 8-layered gauze and the filtrate was centrifuged at 15,000×g for 20 minutes, followed by recovering the middle layer as a crude extract. The crude extract was treated with ammonium sulfate (65% saturation) and the generated precipitates were collected by centrifugation (15,000×g, 20 minutes), followed by dialyzing the precipitates after dissolution against the above-mentioned buffer. After the dialysis, precipitates were eliminated by filtration to obtain ammonium sulfate fraction.

The ammonium sulfate fraction was applied to a column (2.0×10 cm) of DEAE-Cellulose (commercially available from Whattman) equilibrated with buffer A (10 mM Tris-HCl, pH 7, 1 mM $CaCl_2$, 1 mM 2-mercaptoethanol). After washing the column with about 100 ml of buffer A containing 50 mM NaCl, elution was carried out with 120 ml of buffer A having a linear gradient of NaCl concentration from 50 mM to 350 mM. PLD was eluted at a NaCl concentration of about 0.2M. The fraction having PLD activity was collected as an eluted solution (DEAE-cellulose).

To the eluted solution (DEAE-cellulose), 3M ammonium sulfate was added in an amount attaining the final concentration of ammonium sulfate of 1M, and the resulting mixture was applied to a Phenyl Sepharose column (commercially available from Pharmacia, 2.6×10 cm)

equilibrated with buffer A containing 1M ammonium sulfate. Elution was performed using 240 ml of buffer A having a linear gradient of ammonium sulfate concentration from 1.0M to 0M. PLD was eluted at a concentration of ammonium sulfate of about 0.1M. The fraction having the activity was recovered and dialyzed against buffer A to obtain an eluted solution (Phenyl Sepharose).

The eluted solution (Phenyl Sepharose) was applied to Mono Q column (anion-exchange column commercially available from Pharmacia, 16×10 cm) equilibrated with buffer A, and elution was performed using 150 ml of buffer A having a gradient of NaCl concentration from 50 mM to 350 mM. PLD was eluted at NaCl concentration from 210 mM to 235 mM. The fraction having PLD activity was recovered and dialyzed against buffer A to obtain an eluted solution (Mono Q 1st).

The eluted solution (Mono Q 1st) was concentrated to 0.5 ml by ultrafiltration and applied to Superose 6 column (commercially available from Pharmacia, 1.0×30 cm equilibrated with buffer A containing 0.1M NaCl and elution was performed using the same buffer. The molecular weight of PLD was estimated to be 78 kDa. The fraction having PLD activity was recovered as an eluted solution (Superose 6).

To the eluted solution (Superose 6), 2.5 ml of 40% Carrier Ampholite (commercially available from Pharmacia, pH 4.0–6.0) and distilled water were added to attain a final volume of 50 ml and isoelectric electrophoresis was carried out using Rotofore (commercially available from Biorad). Electrophoresis was performed at 2° C. with a constant power of 12 W for 4 hours. PLD activity was observed at about pH 4.9. The fraction having PLD activity was collected and dialyzed against buffer A to obtain an isoelectric electrophoresis fraction.

The isoelectric electrophoresis fraction was applied to Mono Q column (commercially available from Pharmacia, 0.5×5 cm) and eluted with NaCl having a linear gradient of concentration of 50 mM to 350 mM. PLD was eluted at NaCl concentrations of about 210 mM and about 235 mM. The two fractions having PLD activity were recovered as eluted solutions (Mono Q 2nd-I, II).

Purities of the eluted solutions (Mono Q 2nd-I, II) were checked by SDS-polyacrylamide electrophoresis (Laemmli (1970)) using 7.5% acrylamide. After the electrophoresis, the gel was stained with Coomassie brilliant blue R-250. With either eluted solution, a main band was observed at a position corresponding to a molecular weight of 82 kDa. With the eluted solution (Mono Q 2nd-II), only a single band was observed.

By the purification described above, the purification magnifications of the eluted solutions (Mono Q 2nd-I, II) were 380 times and 760 times, respectively, with respect to the crude extract.

Properties of the enzymes contained in the two fractions were determined. The results are shown in Table 1. The buffer solutions used for the measurement of the optimum pH were sodium acetate (pH 4–6), MES-NaOH (pH 5.5–7.0) and Tris-HCl (pH 7–9), all of which have a concentration of 100 mM in all of the buffer solutions. The pH stability means the pH range in which decrease in the enzyme activity is not observed after leaving the enzyme at the respective pH at 25° C. for 30 minutes. The temperature stability was measured by measuring the remaining activity after leaving the enzyme to stand at 4° C., 25° C., 37° C. or 50° C. for 30 minutes. The substrate specificity was measured at a substrate concentration of 5 mM and expressed in terms of the relative activity taking the enzyme activity to phosphatidylcholine as 100.

TABLE 1

|  | Mono Q 2nd-I | Mono Q 2nd-II |
| --- | --- | --- |
| Km Value | 0.29 mM | 0.29 mM |
| Optimum pH | 6 | 6 |
| pH Stability | 7–8 | 7–8 |
| Temperature Stability | 4–37° C. | 4–37° C. |
| $Ca^{2+}$ Dependency | not less than 20 mM | not less than 20 mM |
| Substrate Specificity |  |  |
| Phosphatidylcholine | 100 | 100 |
| Lysophosphatidylcholine | 13 | 12 |
| Sphingomyelin | 6 | 4 |

2. Proof that Purified Protein is PLD

Each of the eluted solutions (Mono Q 2nd-I, II) was subjected to SDS-polyacrylamide gel electrophoresis in the same manner as in the purity test, and the obtained patterns were transferred to PVDF membranes (commercially available from Millipore), followed by staining the membranes. The band of the protein having the molecular weight of 82 kDa was cut out and the amino acid sequence of the N-terminal region of the protein was determined by a protein sequencer (commercially available from Shimazu Seisakusho, PSQ-1) . For both proteins, amino acid sequence up to 10 residues from the N-terminal could be determined, and the determined sequences were identical. The sequence (SEQ ID NO: 8)was as follows.

Val Gly Lys Gly Ala Thr Lys Val Tyr Ser

Although the relationship between the proteins having the molecular weight of 82 kDa contained in the two fractions having the enzyme activity is not clear, it is thought that they have high homology in their amino acid sequences, so that it was judged that there would be no problem even if a mixture of the fractions is used as an antigen for preparing an antibody.

A mixture of the eluted solutions (Mono Q 2nd-I, II) was subjected to SDS-polyacrylamide gel electrophoresis using 7.5% acrylamide, and the gel was stained with Coomassie brilliant blue R-250. The band of the protein having the molecular weight of 82 kDa was cut out and recovered by electroelution (25 mM Tris, 192 mM glycine, 0.025% SDS, 100 V, 10 hours). Then SDS was removed by electrodialysis (15 mM ammonium bicarbonate, 200 V, 5 hours) and the resultant was lyophilized. For the electroelution and electrodialysis, BIOTRAP (commercially available from Schleicher & Schuell) was used.

The protein having the molecular weight of 82 kDa highly purified by the above-described method was administered to a rabbit in an amount of 50 μg per time at 7 days' intervals. Immunological titration test was performed for the sera before the immunization and after the third immunization. To the PLD solution containing $8.6×10^{-3}$ units of PLD, were added 0–50 μl of the serum before the immunization or after the third immunization, 50 μl of 250 mM Tris-HCl (pH7.0), 5 μl of 50 mM $CaCl_2$, 50 μl of 0.2% Triton X-100 (trademark) and water to a total volume of 250 μl, and the mixture was left to stand at room temperature for 2.5 hours. To the resultant, 200 μl of Protein A Sepharose (commercially available from Pharmacia) was added and the resulting mixture was gently shaken at room temperature for 2 hours. The mixture was then centrifuged (500×g, 5 minutes) and the enzyme activity in the supernatant was measured. Taking the measured enzyme activity in the case where the serum was not added as 100%, the enzyme activities in cases where 20 μl and 50 μl of the serum before immunization were added were 95% and 88%, respectively, and the enzyme activities in cases where 20 μl and 50 μl of the serum after the third immunization were added were 75% and 30%, respectively. These results prove that the protein having the molecular weight of 82 kDa is PLD.

3. Determination of Amino Acid Sequence of Internal Regions

The PLD protein was fragmentated in a gel (Cleveland et al., J. Biol. Chem., 252, 1102(1977)). The cut out gel containing the PLD protein was inserted into a stacking gel well on a 15% acrylamide gel prepared for separation of peptides, and *Staphylococcus aureus* V8 protease (commercially available from Wako Pure Chemical Industries, Ltd) in an amount of ⅟₁₀ volume of the PLD protein was overlaid, followed by starting electrophoresis. The electrophoresis was stopped at the time point at which the bromophenol blue reached the center of the stacking gel and then restarted 30 minutes later. After the electrophoresis, the pattern was transferred to a PVDF membrane and the membrane was stained. Clear bands were observed at the positions corresponding to molecular weights of 20, 14, 13, 11 and 10 kDa. Each of the bands of the peptide fragments having molecular weights of 20, 14 and 13 kDa were cut out and their amino acid sequences were determined by a protein sequencer. The determined sequences are as follows.

| | |
|---|---|
| 20 kDa | Asn Tyr Phe His Gly Ser Asp Val Asn ? Val Leu ? Pro Arg Asn Pro Asp Asp (Asp) ? ? |
| 14 kDa | Thr ? Asn Val Gln Leu Phe Arg Ser Ile Asp Gly Gly Ala Ala Phe Gly Phe Pro Asp Thr Pro Glu Glu Ala Ala Lys ? Gly Leu Val Ser Gly (SEQ ID NO:10) |
| 13 kDa | Ile Ala Met Gly Gly Tyr Gln Phe Tyr His Leu Ala Thr Arg Gln Pro Ala Arg Gly Gln Ile His Gly Phe Arg Met Ala Leu ? Tyr Glu His Leu Gly Met Leu ? Asp Val Phe (SEQ ID NO:11) |

In the sequences, "?" means the amino acid residue which could not be identified, and the amino acid residue in parentheses means that the amino acid residue could not be identified confidentially.

4. Preparation of cDNA Library of Rice Immature Seeds

Total RNAs were extracted from immature seeds obtained after 5 days from flowering by the SDS-phenol method, and prepared by the lithium chloride precipitation. Poly(A) ⁺RNA was prepared using Oligotex-dT30 (commercially available from Takara Shuzo) according to the instructions provided by the manufacturer. For the cDNA cloning, cDNA synthesis System Plus (commercially available from Amersham) and cDNA Cloning System λgt10 (commercially available from Amersham) were used. However, λZAPII vector (commercially available from Stratagene) was used as the cloning vector and XL1-Blue was used as the host cells.

5. Preparation of Probes

Oligonucleotides corresponding to the amino acid sequences of PLD were synthesized by a DNA synthesizer (commercially available from Applied Biosystems). The sequences thereof as well as the corresponding amino acid sequences are as follows.

| | |
|---|---|
| 20KF | 5' AAYTAYTTYCAYGG 3'(SEQ ID NO:12) |
| 20KR1 | 5' RTCRTCRTCNGGRTT 3'(SEQ ID NO:13) |

(In these sequences, "R" represents a purine base A or G; "Y" represents a pyrimidine base T or C; and N represents G, A, T or C.)

The 20 KF is a mixture of 32 kinds of oligonucleotides containing the DNA sequences encoding the amino acid sequence of Asn Tyr Phe His Gly (SEQ ID NO: 14)

found in a peptide having a molecular weight of 20 kDa, and the 20 KR1 is a mixture of 128 kinds of oligonucleotides containing complementary chains of the DNA sequences encoding the amino acid sequence of Asn Pro Asp Asp(Asp)(SEQ ID NO:15)

found in the same peptide.

The cDNA synthesis was carried out using 10 ng of Poly(A) ⁺RNA, 0.3 μg of random hexamer (N6), 10 U of an RNase inhibitor (RNA Guard, commercially available from Pharmacia), 1 mM each of dATP, dCTP, dGTP and dTTP, 1×PCR buffer (commercially available from Takara Shuzo), 50 mM of magnesium chloride and 100 U of a reverse transcriptase (M-MuLV RTase, commercially available from BRL) in a total volume of 10 μl. The reaction was carried out at 37° C. for 30 minutes and the reaction mixture was then heated at 95° C. for 5 minutes, followed by retaining the reaction mixture in ice.

Polymerase chain reaction (PCR) was performed using the above-described cDNA as a template and 20 KF and 20 KR1 as primers. The reaction was performed using 10 μl of the cDNA synthesis reaction mixture, a mixture of 50 pmol each of the primers, 200 μM each of dATP, dCTP, dGTP and dTTP, 1×PCR buffer (commercially available from TAKARA SHUZO), and 2.5 U of AmpliTaq DNA polymerase (commercially available from TAKARA SHUZO) in a total volume of 50 μl. A cycle of temperature conditions of 94° C. for 1 minute, 40° C. for 1 minute and 72° C. for 2.5 minutes was repeated 30 times in a DNA Thermocycler (commercially available from Perkin Elmer Cetus).

The PCR product was separated on 2% agarose gel. A small number of fragments were detected by the ethidium bromide staining method. One of them had a size of 94 bp as expected.

The PCR fragment was cut out from the gel and subcloned into pUC19 plasmid. The DNA sequence of the subcloned PCR fragment was determined by the dideoxy method using T7 sequencing kit (commercially available from Pharmacia). Between the two primers, a DNA sequence encoding the expected amino acid sequence was observed. The nucleotide sequence of the DNA between the primers and the amino acid sequence encoded thereby are as follows (SEQ ID NOS: 16 and 17 ).

| |
|---|
| C TCT GAC GTG AAC TGT GTT CTA TGC CCT CGC |
| Ser Asp Val Asn Cys Val Leu Cys Pro Arg |

Isotope ³²P (commercially available from Amersham) was incorporated into the oligonucleotide using a DNA 5'-end labelling kit MEGALABEL (commercially available from Takara Shuzo) to obtain a radioactive oligonucleotide probe.

6. Screening of PLD Gene-containing Clones

Using the radioactive oligonucleotide as a probe, a cDNA library was screened. Hybridization solution contained 0.5M sodium phosphate buffer (pH 7.2), 7% SDS, 1 mM EDTA and 100 μg/ml of salmon sperm DNA, and hybridization was performed after adding the probe to the hybridization solution at 45° C. for 16 hours. The washing solution contained 0.3M NaCl and 30 mM sodium citrate, and washing was performed twice at 45° C. for 20 minutes each. Positive plaques were isolated and subcloned in vivo into pBluescript plasmid (commercially available from Stratagene) in accordance with the instructions provided by the manufacturer of λZAPII cloning vector. The nucleotide sequence was determined by the dideoxy method. As a result, a region encoding the internal amino acid sequence determined in the "Section 3" existed.

7. Determination of Nucleotide Sequence of 5'-end Region

Since a clone containing the full length of cDNA could not be isolated, a DNA fragment having the 5'-end region was prepared by RACE method (Edwards et al., Nucleic Acids Res., 19, 5227–5232 (1991)). 5'-AmpliFINDER RACE Kit (commercially available from Clonetech) was used in accordance with the manual attached to the product. An oligoDNA was synthesized based on the nucleotide sequence of the cDNA determined in "Section 6", and PCR was performed using the mRNA prepared by the method described in "Section 4" as a template. The PCR product was subcloned into a PCRII vector (commercially available from Invitrogen) and the nucleotide sequence was determined by the dideoxy method. The thus determined nucleotide sequence of the cDNA of rice PLD as well as the deduced amino acid sequence encoded thereby is shown in SEQ ID NOS: 2 and 3 in the Sequence Listing. It is thought that translation is initiated from the 182nd nucleotide shown in SEQ ID NO. 2 since a termination codon exists at 36 bases upstream thereof.

8. Isolation of PLD Genomic Clone Corresponding to PLD cDNA and Identification of Promoter Region To isolate a genomic DNA clone having the regulatory sequence of the PLD gene corresponding to the PLD cDNA determined in "section 6", which was cloned into pBluescript plasmid, a genomic library of rice, variety "KOSHIHIKARI" was prepared. This was carried out by partially digesting DNAs from live leaves of KOSHIHIKARI with Mbo I, purifying a fraction having a size of 16–20 kb by sucrose gradient centrifugation, and using lambda DASH II (commercially available from Stratagene) and GigapackII Gold (commercially available from Stratagene). The genomic library was screened with the PLD cDNA clone as a probe. The screening was carried out in the same manner as in "Section 6" except that hybridization was performed at 65° C. for 16 hours, the washing solution contained 0.5×SSC and 0.1% SDS, and that the washing was performed twice at 65° C. for 20 minutes each. The nucleotide sequence of the hybridized genomic clone was determined by the dideoxy method. As a result, a region homologous to the cDNA sequence determined in "Section 6" existed.

The transcription initiation site was determined by the method described in "Section 7". In the vicinity of the transcription initiation site, a "TATA" consensus sequence box was observed. The ATG translation initiation site was determined based on the determined DNA sequence as the most upstream ATG codon in the translation open reading frame of the clone and as the ATG codon which is first accessible in the mRNA synthesized in rice.

The DNA sequence of a part of the genomic clone hybridized with the cDNA clone is shown in SEQ ID NO: 4. In the genomic DNA sequence, an open reading frame starting from the ATG translation initiation codon, which overlaps with the corresponding cDNA sequence has been identified. The promoter region exists upstream of the ATG translation initiation codon and starts from the site immediately upstream thereof.

Figure 1:
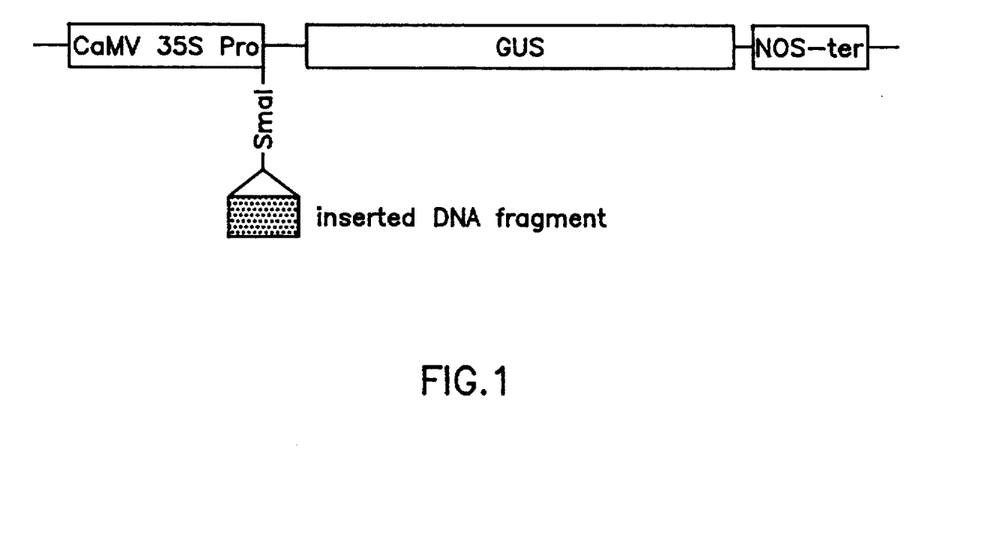
FIG. 1 shows the important part of a genetic map of pBI221 into which the DNA fragment according to the present invention is inserted, which was prepared in the Example of the present invention.

9. Identification of Introns and Analysis of Functions thereof on Expression of Genes From comparison between the cDNA (SEQ ID NO. 2) and the genomic DNA (SEQ ID NO. 4), it was proved that 3 introns exist in PLD gene. Among these, the intron having a size of 173 bp located at the 5'-flanking region of the mRNA (i.e., the nucleotide sequence between 1666nt and 1838nt of the nucleotide sequence shown in SEQ ID NO: 4, the sequence being shown in SEQ ID NO: 7) was tested for its influence on expression of a gene in plant cells. Primers of 15mer each of which contains 5 bases of exon region (5'-ACCCGGTAAGCCCAG-3', 3'-CCCCCGCGTCCATCC-5') (SEQ ID NOS: 18 and 19) were synthesized and PCR was carried out using the genomic clone as a template according to the method described in the Section of "5. Preparation of Probes". The PCR product was subcloned into PCRII vector and a fragment was cut out with Eco RI. The fragment was blunted and inserted into the Sma I site of a plasmid pBI221 (commercially available from Toyobo) (see FIG. 1). The obtained recombinant plasmid was introduced into rice cultured cells (Baba et al., Plant Cell Physiol. 27, 463–471 (1986)) in accordance with the reported method (Shimamoto et al., Nature, 338, 274–276 (1989)) and β-glucuronidase (GUS) activity was measured. As shown in Table 2, by introducing the intron, the GUS activity was increased. Further, as shown in Table 3, increase in the GUS activity was also observed in the case where the intron was inserted in the reverse direction. The direction of the intron was determined based on the sizes of the fragments cut out with Bgl II and Bam HI, utilizing the Bgl II site existing in the intron sequence and the Bam HI site existing in pBI221.

TABLE 2

| Plasmid | GUS Activity |
|---|---|
| pBI221 | 10.4 |
| pBI221 + intron | 105.7 |

(pmol MU/min./mg protein)

TABLE 3

| Plasmid | GUS Activity |
|---|---|
| pBI221 | 8.8 |
| pBI221 + intron | 79.4 |
| pBI221 + intron (reverse direction) | 54.2 |

(pmol MU/min./mg protein)

We claim:

1. A DNA fragment comprising the nucleotide sequence of SEQ ID NO:1.

2. A recombinant vector comprising said DNA fragment according to claim 1 and a foreign gene to be expressed, which is operably linked to said DNA fragment at a downstream region of said DNA fragment.

3. A method for expressing a foreign gene comprising introducing said recombinant vector according to claim 2 into host cells and expressing said foreign gene.

4. The method according to claim 3, wherein said DNA fragment has a nucleotide sequence shown in SEQ ID NO:1 in Sequence Listing.

5. The method according to claim 3, wherein said DNA fragment has a nucleotide sequence shown in SEQ ID NO:7 in Sequence Listing.

6. The recombinant vector according to claim 2, wherein said DNA fragment has a nucleotide sequence shown in SEQ ID NO:7.

7. The recombinant vector according to claim 6, wherein said DNA fragment has a nucleotide sequence shown in SEQ ID NO:7 in Sequence Listing.

8. A DNA fragment comprising the nucleotide sequence of SEQ ID NO:7.

9. A recombinant vector comprising said DNA fragment according to claim 8 and a foreign gene to be expressed, which is operably linked to said DNA fragment at a downstream region of said DNA fragment.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 183 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

```
ACCCGGTAAG CCCAGTGTGC TTAGGCTAAG CGCACTAGAG CTTCTTGCTC GCTTGCTTCT      60
TCTCCGCTCA GATCTGCTTG CTTGCTTGCT TCGCTAGAAC CCTACTCTGT GCTGCGAGTG     120
TCGCTGCTTC GTCTTCCTTC CTCAAGTTCG ATCTGATTGT GTGTGTGGGG GGGCGCAGGT     180
AGG                                                                  183
```

( 2 ) INFORMATION FOR SEQ ID NO:2:

( i ) SEQUENCE CHARACTERISTICS:
        ( A ) LENGTH: 3040 base pairs
        ( B ) TYPE: nucleic acid
        ( C ) STRANDEDNESS: single
        ( D ) TOPOLOGY: linear     ( i i ) MOLECULE TYPE: cDNA to mRNA     ( i x ) FEATURE:
        ( A ) NAME/KEY: CDS
        ( B ) LOCATION: 182..2617

( x i ) SEQUENCE DESCRIPTION: SEQ ID NO:2:

```
AGTCTCTCTT CTCCCGCAAT TTTATAATCT CGATCGATCC AATCTGCTCC CCTTCTTCTT      60
CTACTCTCCC CATCTCGGCT CTCGCCATCG CCATCCTCCT CTCCCTTCCC GGAGAAGACG     120
CCTCCCTCCG CCGATCACCA CCCGGTAGGG CGAGGAGGGA GCCAAATCCA AATCAGCAGC     180

C ATG GCG CAG ATG CTG CTC CAT GGG ACG CTG CAC GCC ACC ATC TTC         226
  Met Ala Gln Met Leu Leu His Gly Thr Leu His Ala Thr Ile Phe
   1               5                  10                  15

GAG GCG GCG TCG CTC TCC AAC CCG CAC CGC GCC AGC GGA AGC GCC CCC       274
Glu Ala Ala Ser Leu Ser Asn Pro His Arg Ala Ser Gly Ser Ala Pro
                 20                  25                  30

AAG TTC ATC CGC AAG TTT GTG GAG GGG ATT GAG GAC ACT GTG GGT GTC       322
Lys Phe Ile Arg Lys Phe Val Glu Gly Ile Glu Asp Thr Val Gly Val
             35                  40                  45

GGC AAA GGC GCC ACC AAG GTG TAT TCT ACC ATT GAT CTG GAG AAA GCT       370
Gly Lys Gly Ala Thr Lys Val Tyr Ser Thr Ile Asp Leu Glu Lys Ala
         50                  55                  60

CGT GTA GGG CGA ACT AGG ATG ATA ACC AAT GAG CCC ATC AAC CCT CGC       418
Arg Val Gly Arg Thr Arg Met Ile Thr Asn Glu Pro Ile Asn Pro Arg
     65                  70                  75

TGG TAT GAG TCG TTC CAC ATC TAT TGC GCT CAT ATG GCT TCC AAT GTG       466
Trp Tyr Glu Ser Phe His Ile Tyr Cys Ala His Met Ala Ser Asn Val
 80                  85                  90                  95

ATC TTC ACT GTC AAG ATT GAT AAC CCT ATT GGG GCA ACG AAT ATT GGG       514
Ile Phe Thr Val Lys Ile Asp Asn Pro Ile Gly Ala Thr Asn Ile Gly
                100                 105                 110

AGG GCT TAC CTG CCT GTC CAA GAG CTT CTC AAT GGA GAG GAG ATT GAC       562
Arg Ala Tyr Leu Pro Val Gln Glu Leu Leu Asn Gly Glu Glu Ile Asp
            115                 120                 125

AGA TGG CTC GAT ATC TGT GAT AAT AAC CGC GAG TCT GTT GGT GAG AGC       610
Arg Trp Leu Asp Ile Cys Asp Asn Asn Arg Glu Ser Val Gly Glu Ser
        130                 135                 140

AAG ATC CAT GTG AAG CTT CAG TAC TTC GAT GTT TCC AAG GAT CGC AAT       658
```

-continued

| | | | | | | | | | | | | | | | |
|---|---|---|---|---|---|---|---|---|---|---|---|---|---|---|---|
| Lys | Ile | His | Val | Lys | Leu | Gln | Tyr | Phe | Asp | Val | Ser | Lys | Asp | Arg | Asn |
| | 145 | | | | 150 | | | | | 155 | | | | | |

| TGG | GCG | AGG | GGT | GTC | CGC | AGT | ACC | AAG | TAT | CCA | GGT | GTT | CCT | TAC | ACC | 706 |
|---|---|---|---|---|---|---|---|---|---|---|---|---|---|---|---|---|
| Trp | Ala | Arg | Gly | Val | Arg | Ser | Thr | Lys | Tyr | Pro | Gly | Val | Pro | Tyr | Thr | |
| 160 | | | | | 165 | | | | | 170 | | | | | 175 | |

| TTC | TTC | TCT | CAG | AGG | CAA | GGG | TGC | AAA | GTT | ACC | TTG | TAC | CAA | GAT | GCT | 754 |
|---|---|---|---|---|---|---|---|---|---|---|---|---|---|---|---|---|
| Phe | Phe | Ser | Gln | Arg | Gln | Gly | Cys | Lys | Val | Thr | Leu | Tyr | Gln | Asp | Ala | |
| | | | | 180 | | | | | 185 | | | | | 190 | | |

| CAT | GTC | CCA | GAC | AAC | TTC | ATT | CCA | AAG | ATT | CCG | CTT | GCC | GAT | GGC | AAG | 802 |
|---|---|---|---|---|---|---|---|---|---|---|---|---|---|---|---|---|
| His | Val | Pro | Asp | Asn | Phe | Ile | Pro | Lys | Ile | Pro | Leu | Ala | Asp | Gly | Lys | |
| | | | 195 | | | | | 200 | | | | | 205 | | | |

| AAT | TAT | GAA | CCC | CAC | AGA | TGC | TGG | GAG | GAT | ATC | TTT | GAT | GCT | ATA | AGC | 850 |
|---|---|---|---|---|---|---|---|---|---|---|---|---|---|---|---|---|
| Asn | Tyr | Glu | Pro | His | Arg | Cys | Trp | Glu | Asp | Ile | Phe | Asp | Ala | Ile | Ser | |
| | | 210 | | | | | 215 | | | | | 220 | | | | |

| AAT | GCT | CAA | CAT | TTG | ATT | TAC | ATC | ACT | GGC | TGG | TCT | GTA | TAC | ACT | GAG | 898 |
|---|---|---|---|---|---|---|---|---|---|---|---|---|---|---|---|---|
| Asn | Ala | Gln | His | Leu | Ile | Tyr | Ile | Thr | Gly | Trp | Ser | Val | Tyr | Thr | Glu | |
| 225 | | | | | 230 | | | | | 235 | | | | | | |

| ATC | ACC | TTG | GTT | AGG | GAC | TCC | AAT | CGT | CCA | AAA | CCT | GGA | GGG | GAT | GTC | 946 |
|---|---|---|---|---|---|---|---|---|---|---|---|---|---|---|---|---|
| Ile | Thr | Leu | Val | Arg | Asp | Ser | Asn | Arg | Pro | Lys | Pro | Gly | Gly | Asp | Val | |
| 240 | | | | | 245 | | | | | 250 | | | | | 255 | |

| ACC | CTT | GGG | GAG | TTG | CTC | AAG | AAG | AAG | GCC | AGT | GAA | GGT | GTT | CGG | GTC | 994 |
|---|---|---|---|---|---|---|---|---|---|---|---|---|---|---|---|---|
| Thr | Leu | Gly | Glu | Leu | Leu | Lys | Lys | Lys | Ala | Ser | Glu | Gly | Val | Arg | Val | |
| | | | | 260 | | | | | 265 | | | | | 270 | | |

| CTC | ATG | CTT | GTG | TGG | GAT | GAC | AGG | ACT | TCA | GTT | GGT | TTG | CTA | AAG | AGG | 1042 |
|---|---|---|---|---|---|---|---|---|---|---|---|---|---|---|---|---|
| Leu | Met | Leu | Val | Trp | Asp | Asp | Arg | Thr | Ser | Val | Gly | Leu | Leu | Lys | Arg | |
| | | | 275 | | | | | 280 | | | | | 285 | | | |

| GAT | GGC | TTG | ATG | GCA | ACA | CAT | GAT | GAG | GAA | ACT | GAA | AAT | TAC | TTC | CAT | 1090 |
|---|---|---|---|---|---|---|---|---|---|---|---|---|---|---|---|---|
| Asp | Gly | Leu | Met | Ala | Thr | His | Asp | Glu | Glu | Thr | Glu | Asn | Tyr | Phe | His | |
| | | 290 | | | | | 295 | | | | | 300 | | | | |

| GGC | TCT | GAC | GTG | AAC | TGT | GTT | CTA | TGC | CCT | CGC | AAC | CCT | GAT | GAC | TCA | 1138 |
|---|---|---|---|---|---|---|---|---|---|---|---|---|---|---|---|---|
| Gly | Ser | Asp | Val | Asn | Cys | Val | Leu | Cys | Pro | Arg | Asn | Pro | Asp | Asp | Ser | |
| | 305 | | | | | 310 | | | | | 315 | | | | | |

| GGC | AGC | ATT | GTT | CAG | GAT | CTG | TCG | ATC | TCA | ACT | ATG | TTT | ACA | CAC | CAT | 1186 |
|---|---|---|---|---|---|---|---|---|---|---|---|---|---|---|---|---|
| Gly | Ser | Ile | Val | Gln | Asp | Leu | Ser | Ile | Ser | Thr | Met | Phe | Thr | His | His | |
| 320 | | | | | 325 | | | | | 330 | | | | | 335 | |

| CAG | AAG | ATA | GTA | GTT | GTT | GAC | CAT | GAG | TTG | CCA | AAC | CAG | GGC | TCC | CAA | 1234 |
|---|---|---|---|---|---|---|---|---|---|---|---|---|---|---|---|---|
| Gln | Lys | Ile | Val | Val | Val | Asp | His | Glu | Leu | Pro | Asn | Gln | Gly | Ser | Gln | |
| | | | | 340 | | | | | 345 | | | | | 350 | | |

| CAA | AGG | AGG | ATA | GTC | AGT | TTC | GTT | GGT | GGC | CTT | GAT | CTC | TGT | GAT | GGA | 1282 |
|---|---|---|---|---|---|---|---|---|---|---|---|---|---|---|---|---|
| Gln | Arg | Arg | Ile | Val | Ser | Phe | Val | Gly | Gly | Leu | Asp | Leu | Cys | Asp | Gly | |
| | | | 355 | | | | | 360 | | | | | 365 | | | |

| AGG | TAT | GAC | ACT | CAG | TAC | CAT | TCT | TTG | TTT | AGG | ACA | CTC | GAC | AGT | ACC | 1330 |
|---|---|---|---|---|---|---|---|---|---|---|---|---|---|---|---|---|
| Arg | Tyr | Asp | Thr | Gln | Tyr | His | Ser | Leu | Phe | Arg | Thr | Leu | Asp | Ser | Thr | |
| | | 370 | | | | | 375 | | | | | 380 | | | | |

| CAT | CAT | GAT | GAC | TTC | CAC | CAG | CCA | AAC | TTT | GCC | ACT | GCA | TCA | ATC | AAA | 1378 |
|---|---|---|---|---|---|---|---|---|---|---|---|---|---|---|---|---|
| His | His | Asp | Asp | Phe | His | Gln | Pro | Asn | Phe | Ala | Thr | Ala | Ser | Ile | Lys | |
| | 385 | | | | | 390 | | | | | 395 | | | | | |

| AAG | GGT | GGA | CCT | AGA | GAG | CCA | TGG | CAT | GAT | ATT | CAC | TCA | CGG | CTG | GAA | 1426 |
|---|---|---|---|---|---|---|---|---|---|---|---|---|---|---|---|---|
| Lys | Gly | Gly | Pro | Arg | Glu | Pro | Trp | His | Asp | Ile | His | Ser | Arg | Leu | Glu | |
| 400 | | | | | 405 | | | | | 410 | | | | | 415 | |

| GGG | CCA | ATC | GCA | TGG | GAT | GTT | CTT | TAC | AAT | TTC | GAG | CAG | AGA | TGG | AGA | 1474 |
|---|---|---|---|---|---|---|---|---|---|---|---|---|---|---|---|---|
| Gly | Pro | Ile | Ala | Trp | Asp | Val | Leu | Tyr | Asn | Phe | Glu | Gln | Arg | Trp | Arg | |
| | | | | 420 | | | | | 425 | | | | | 430 | | |

| AAG | CAG | GGT | GGT | AAG | GAT | CTC | CTT | CTG | CAG | CTC | AGG | GAT | CTG | TCT | GAC | 1522 |
|---|---|---|---|---|---|---|---|---|---|---|---|---|---|---|---|---|
| Lys | Gln | Gly | Gly | Lys | Asp | Leu | Leu | Leu | Gln | Leu | Arg | Asp | Leu | Ser | Asp | |
| | | | 435 | | | | | 440 | | | | | 445 | | | |

| ACT | ATT | ATT | CCA | CCT | TCT | CCT | GTT | ATG | TTT | CCA | GAG | GAC | AGA | GAA | ACA | 1570 |
|---|---|---|---|---|---|---|---|---|---|---|---|---|---|---|---|---|
| Thr | Ile | Ile | Pro | Pro | Ser | Pro | Val | Met | Phe | Pro | Glu | Asp | Arg | Glu | Thr | |
| | | 450 | | | | | 455 | | | | | 460 | | | | |

| TGG | AAT | GTT | CAG | CTA | TTT | AGA | TCC | ATT | GAT | GGT | GGT | GCT | GCT | TTT | GGG | 1618 |
|---|---|---|---|---|---|---|---|---|---|---|---|---|---|---|---|---|

|  |  |  |  |  |  |  |  |  |  |  |  |  |  |  |  |
|---|---|---|---|---|---|---|---|---|---|---|---|---|---|---|---|
| Trp | Asn | Val | Gln | Leu | Phe | Arg | Ser | Ile | Asp | Gly | Gly | Ala | Ala | Phe | Gly |
| 465 |  |  |  |  | 470 |  |  |  |  | 475 |  |  |  |  |  |

| TTC | CCT | GAT | ACC | CCT | GAG | GAG | GCT | GCA | AAA | GCT | GGG | CTT | GTA | AGC | GGA | 1666 |
|---|---|---|---|---|---|---|---|---|---|---|---|---|---|---|---|---|
| Phe | Pro | Asp | Thr | Pro | Glu | Glu | Ala | Ala | Lys | Ala | Gly | Leu | Val | Ser | Gly |  |
| 480 |  |  |  |  | 485 |  |  |  |  | 490 |  |  |  |  | 495 |  |

| AAG | GAT | CAA | ATC | ATT | GAC | AGG | AGC | ATC | CAG | GAT | GCA | TAC | ATA | CAT | GCC | 1714 |
|---|---|---|---|---|---|---|---|---|---|---|---|---|---|---|---|---|
| Lys | Asp | Gln | Ile | Ile | Asp | Arg | Ser | Ile | Gln | Asp | Ala | Tyr | Ile | His | Ala |  |
|  |  |  |  |  | 500 |  |  |  | 505 |  |  |  |  |  | 510 |  |

| ATC | CGG | AGG | GCA | AAG | AAC | TTC | ATC | TAT | ATA | GAG | AAC | CAA | TAC | TTC | CTT | 1762 |
|---|---|---|---|---|---|---|---|---|---|---|---|---|---|---|---|---|
| Ile | Arg | Arg | Ala | Lys | Asn | Phe | Ile | Tyr | Ile | Glu | Asn | Gln | Tyr | Phe | Leu |  |
|  |  |  |  | 515 |  |  |  |  | 520 |  |  |  |  | 525 |  |  |

| GGA | AGT | TCC | TAT | GCC | TGG | AAA | CCC | GAG | GGC | ATC | AAG | CCT | GAA | GAC | ATT | 1810 |
|---|---|---|---|---|---|---|---|---|---|---|---|---|---|---|---|---|
| Gly | Ser | Ser | Tyr | Ala | Trp | Lys | Pro | Glu | Gly | Ile | Lys | Pro | Glu | Asp | Ile |  |
|  |  | 530 |  |  |  |  | 535 |  |  |  |  |  | 540 |  |  |  |

| GGT | GCC | CTG | CAT | TTG | ATT | CCT | AAG | GAG | CTT | GCA | CTG | AAA | GTT | GTC | AGT | 1858 |
|---|---|---|---|---|---|---|---|---|---|---|---|---|---|---|---|---|
| Gly | Ala | Leu | His | Leu | Ile | Pro | Lys | Glu | Leu | Ala | Leu | Lys | Val | Val | Ser |  |
|  | 545 |  |  |  |  | 550 |  |  |  |  | 555 |  |  |  |  |  |

| AAG | ATT | GAA | GCC | GGG | GAA | CGG | TTC | ACT | GTT | TAT | GTT | GTG | GTG | CCA | ATG | 1906 |
|---|---|---|---|---|---|---|---|---|---|---|---|---|---|---|---|---|
| Lys | Ile | Glu | Ala | Gly | Glu | Arg | Phe | Thr | Val | Tyr | Val | Val | Val | Pro | Met |  |
| 560 |  |  |  |  | 565 |  |  |  |  | 570 |  |  |  |  | 575 |  |

| TGG | CCT | GAG | GGT | GTT | CCA | GAG | AGT | GGA | TCT | GTT | CAG | GCA | ATC | CTG | GAC | 1954 |
|---|---|---|---|---|---|---|---|---|---|---|---|---|---|---|---|---|
| Trp | Pro | Glu | Gly | Val | Pro | Glu | Ser | Gly | Ser | Val | Gln | Ala | Ile | Leu | Asp |  |
|  |  |  |  | 580 |  |  |  |  | 585 |  |  |  |  | 590 |  |  |

| TGG | CAA | AGG | AGA | ACA | ATG | GAG | ATG | ATG | TAC | ACT | GAC | ATT | ACA | GAG | GCT | 2002 |
|---|---|---|---|---|---|---|---|---|---|---|---|---|---|---|---|---|
| Trp | Gln | Arg | Arg | Thr | Met | Glu | Met | Met | Tyr | Thr | Asp | Ile | Thr | Glu | Ala |  |
|  |  |  | 595 |  |  |  |  | 600 |  |  |  |  | 605 |  |  |  |

| CTC | CAA | GCC | AAG | GGA | ATT | GAA | GCG | AAC | CCC | AAG | GAC | TAC | CTC | ACT | TTC | 2050 |
|---|---|---|---|---|---|---|---|---|---|---|---|---|---|---|---|---|
| Leu | Gln | Ala | Lys | Gly | Ile | Glu | Ala | Asn | Pro | Lys | Asp | Tyr | Leu | Thr | Phe |  |
|  |  | 610 |  |  |  |  | 615 |  |  |  |  | 620 |  |  |  |  |

| TTC | TGC | TTG | GGT | AAC | CGT | GAG | GTG | AAG | CAG | GCT | GGG | GAA | TAT | CAG | CCT | 2098 |
|---|---|---|---|---|---|---|---|---|---|---|---|---|---|---|---|---|
| Phe | Cys | Leu | Gly | Asn | Arg | Glu | Val | Lys | Gln | Ala | Gly | Glu | Tyr | Gln | Pro |  |
| 625 |  |  |  |  | 630 |  |  |  |  | 635 |  |  |  |  |  |  |

| GAA | GAA | CAA | CCA | GAA | GCT | GAC | ACT | GAT | TAC | AGC | CGA | GCT | CAG | GAA | GCT | 2146 |
|---|---|---|---|---|---|---|---|---|---|---|---|---|---|---|---|---|
| Glu | Glu | Gln | Pro | Glu | Ala | Asp | Thr | Asp | Tyr | Ser | Arg | Ala | Gln | Glu | Ala |  |
| 640 |  |  |  |  | 645 |  |  |  |  | 650 |  |  |  |  | 655 |  |

| AGG | AGG | TTC | ATG | ATC | TAT | GTC | CAC | ACC | AAA | ATG | ATG | ATA | GTT | GAC | GAT | 2194 |
|---|---|---|---|---|---|---|---|---|---|---|---|---|---|---|---|---|
| Arg | Arg | Phe | Met | Ile | Tyr | Val | His | Thr | Lys | Met | Met | Ile | Val | Asp | Asp |  |
|  |  |  |  | 660 |  |  |  |  | 665 |  |  |  |  | 670 |  |  |

| GAG | TAC | ATC | ATC | ATC | GGT | TCT | GCA | AAC | ATC | AAC | CAG | AGG | TCG | ATG | GAC | 2242 |
|---|---|---|---|---|---|---|---|---|---|---|---|---|---|---|---|---|
| Glu | Tyr | Ile | Ile | Ile | Gly | Ser | Ala | Asn | Ile | Asn | Gln | Arg | Ser | Met | Asp |  |
|  |  |  | 675 |  |  |  |  | 680 |  |  |  |  | 685 |  |  |  |

| GGC | GCT | AGG | GAC | TCT | GAG | ATC | GCC | ATG | GGC | GGG | TAC | CAG | CCA | TAC | CAT | 2290 |
|---|---|---|---|---|---|---|---|---|---|---|---|---|---|---|---|---|
| Gly | Ala | Arg | Asp | Ser | Glu | Ile | Ala | Met | Gly | Gly | Tyr | Gln | Pro | Tyr | His |  |
|  |  | 690 |  |  |  |  | 695 |  |  |  |  | 700 |  |  |  |  |

| CTG | GCG | ACC | AGG | CAA | CCA | GCC | CGT | GGC | CAG | ATC | CAT | GGC | TTC | CGG | ATG | 2338 |
|---|---|---|---|---|---|---|---|---|---|---|---|---|---|---|---|---|
| Leu | Ala | Thr | Arg | Gln | Pro | Ala | Arg | Gly | Gln | Ile | His | Gly | Phe | Arg | Met |  |
|  | 705 |  |  |  |  | 710 |  |  |  |  | 715 |  |  |  |  |  |

| GCG | CTG | TGG | TAC | GAG | CAC | CTG | GGA | ATG | CTG | GAT | GAT | GTG | TTC | CAG | CGC | 2386 |
|---|---|---|---|---|---|---|---|---|---|---|---|---|---|---|---|---|
| Ala | Leu | Trp | Tyr | Glu | His | Leu | Gly | Met | Leu | Asp | Asp | Val | Phe | Gln | Arg |  |
| 720 |  |  |  |  | 725 |  |  |  |  | 730 |  |  |  |  | 735 |  |

| CCC | GAG | AGC | CTG | GAG | TGT | GTG | CAG | AAG | GTG | AAC | AGG | ATC | GCG | GAG | AAG | 2434 |
|---|---|---|---|---|---|---|---|---|---|---|---|---|---|---|---|---|
| Pro | Glu | Ser | Leu | Glu | Cys | Val | Gln | Lys | Val | Asn | Arg | Ile | Ala | Glu | Lys |  |
|  |  |  | 740 |  |  |  |  | 745 |  |  |  |  | 750 |  |  |  |

| TAC | TGG | GAC | ATG | TAC | TCC | AGC | GAC | GAC | CTC | CAG | CAG | GAC | CTC | CCT | GGC | 2482 |
|---|---|---|---|---|---|---|---|---|---|---|---|---|---|---|---|---|
| Tyr | Trp | Asp | Met | Tyr | Ser | Ser | Asp | Asp | Leu | Gln | Gln | Asp | Leu | Pro | Gly |  |
|  |  |  | 755 |  |  |  |  | 760 |  |  |  |  | 765 |  |  |  |

| CAC | CTC | CTC | AGC | TAC | CCC | ATT | GGC | GTC | GCC | AGC | GAT | GGT | GTG | GTG | ACT | 2530 |
|---|---|---|---|---|---|---|---|---|---|---|---|---|---|---|---|---|
| His | Leu | Leu | Ser | Tyr | Pro | Ile | Gly | Val | Ala | Ser | Asp | Gly | Val | Val | Thr |  |
|  |  | 770 |  |  |  |  | 775 |  |  |  |  | 780 |  |  |  |  |

| GAG | CTG | CCC | GGG | ATG | GAG | TAC | TTT | CCT | GAC | ACA | CGG | GCC | CGC | GTC | CTC | 2578 |
|---|---|---|---|---|---|---|---|---|---|---|---|---|---|---|---|---|

|     |     |     |     |     |     |     |     |     |     |     |     |     |     |     |
| --- | --- | --- | --- | --- | --- | --- | --- | --- | --- | --- | --- | --- | --- | --- |
| Glu | Leu | Pro | Gly | Met | Glu | Tyr | Phe | Pro | Asp | Thr | Arg | Ala | Arg | Val | Leu |
|     | 785 |     |     |     | 790 |     |     |     |     | 795 |     |     |     |     |     |

```
GGC GCC AAG TCG GAT TAC ATG CCC CCC ATC CTC ACC TCA TAGACGAGGA       2627
Gly Ala Lys Ser Asp Tyr Met Pro Pro Ile Leu Thr Ser
800             805                 810

AGCACTACAC TACAATCTGC TGGCTTCTCC TGTCAGTCCT TCTGTACTTC TTCAGTTTGG    2687

TGGCGAGATG GTATGGCCGT TGTTCAGAAT TTCTTCAGAA TAGCAGTTGT TACAGTTGTG    2747

AATCATAAAG TAATAAGTGC AGTATCTGTG CATGGTTGAG TTGGGAAGAA GATCGGGGAT    2807

GCAATGATGC TTGTGAAGTT GTGATGCCGT TTGTAAGATG GGAAGTTGGG AACTACTAAG    2867

TAATTGGCAT GATTGTACTT TGCACTACTG TTTAGCGTTG TTGATACTGG TTAACCGTGT    2927

GTTCATCTGA ACTTGATTCT TGATGCAGTT TGTGGCATTA CCAGTTTATC ATCGTTCTTC    2987

AGGAAAAAAA AAAAAAAAAA AAAAAAAAAA AAAAAAAAAA AAAAAAAAAA AAA           3040
```

( 2 ) INFORMATION FOR SEQ ID NO:3:

( i ) SEQUENCE CHARACTERISTICS:
        ( A ) LENGTH: 812 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:3:

```
Met Ala Gln Met Leu Leu His Gly Thr Leu His Ala Thr Ile Phe Gln
 1               5                  10                  15

Ala Ala Ser Leu Ser Asn Pro His Arg Ala Ser Gly Ser Ala Pro Lys
                20                  25                  30

Phe Ile Arg Lys Phe Val Glu Gly Ile Glu Asp Thr Val Gly Val Gly
            35                  40                  45

Lys Gly Ala Thr Lys Val Tyr Ser Thr Ile Asp Leu Glu Lys Ala Arg
        50                  55                  60

Val Gly Arg Thr Arg Met Ile Thr Asn Glu Pro Ile Asn Pro Arg Trp
 65                  70                  75                  80

Tyr Glu Ser Phe His Ile Tyr Cys Ala His Met Ala Ser Asn Val Ile
                85                  90                  95

Phe Thr Val Lys Ile Asp Asn Pro Ile Gly Ala Thr Asn Ile Gly Arg
                100                 105                 110

Ala Tyr Leu Pro Val Gln Glu Leu Leu Asn Gly Gln Glu Ile Asp Arg
            115                 120                 125

Trp Leu Asp Ile Cys Asp Asn Asn Arg Glu Ser Val Gly Glu Ser Lys
130                 135                 140

Ile His Val Lys Leu Gln Tyr Phe Asp Val Ser Lys Asp Arg Asn Trp
145                 150                 155                 160

Ala Arg Gly Val Arg Ser Thr Lys Tyr Pro Gly Val Pro Tyr Thr Phe
                165                 170                 175

Phe Ser Gln Arg Gln Gly Cys Lys Val Thr Leu Tyr Gln Asp Ala His
            180                 185                 190

Val Pro Asp Asn Phe Ile Pro Lys Ile Pro Leu Ala Asp Gly Lys Asn
            195                 200                 205

Tyr Glu Pro His Arg Cys Trp Glu Asp Ile Phe Asp Ala Ile Ser Asn
210                 215                 220

Ala Gln His Leu Ile Tyr Ile Thr Gly Trp Ser Val Tyr Thr Glu Ile
225                 230                 235                 240

Thr Leu Val Arg Asp Ser Asn Arg Pro Lys Pro Gly Gly Asp Val Thr
                245                 250                 255
```

```
Leu Gly Glu Leu Leu Lys Lys Lys Ala Ser Glu Gly Val Arg Val Leu
            260                 265                 270
Met Leu Val Trp Asp Asp Arg Thr Ser Val Gly Leu Leu Lys Arg Asp
        275                 280                 285
Gly Leu Met Ala Thr His Asp Glu Thr Glu Asn Tyr Phe His Gly
    290                 295                 300
Ser Asp Val Asn Cys Val Leu Cys Pro Arg Asn Pro Asp Asp Ser Gly
305                 310                 315                 320
Ser Ile Val Gln Asp Leu Ser Ile Ser Thr Met Phe Thr His His Gln
            325                 330                 335
Lys Ile Val Val Val Asp His Glu Leu Pro Asn Gln Gly Ser Gln Gln
            340                 345                 350
Arg Arg Ile Val Ser Phe Val Gly Gly Leu Asp Leu Cys Asp Gly Arg
            355                 360                 365
Tyr Asp Thr Gln Tyr His Ser Leu Phe Arg Thr Leu Asp Ser Thr His
    370                 375                 380
His Asp Asp Phe His Gln Pro Asn Phe Ala Thr Ala Ser Ile Lys Lys
385                 390                 395                 400
Gly Gly Pro Arg Glu Pro Trp His Asp Ile His Ser Arg Leu Glu Gly
                405                 410                 415
Pro Ile Ala Trp Asp Val Leu Tyr Asn Phe Glu Gln Arg Trp Arg Lys
            420                 425                 430
Gln Gly Gly Lys Asp Leu Leu Leu Gln Leu Arg Asp Leu Ser Asp Thr
            435                 440                 445
Ile Ile Pro Pro Ser Pro Val Met Phe Pro Glu Asp Arg Glu Thr Trp
450                 455                 460
Asn Val Gln Leu Phe Arg Ser Ile Asp Gly Gly Ala Ala Phe Gly Phe
465                 470                 475                 480
Pro Asp Thr Pro Glu Glu Ala Ala Lys Ala Gly Leu Val Ser Gly Lys
                485                 490                 495
Asp Gln Ile Ile Asp Arg Ser Ile Gln Asp Ala Tyr Ile His Ala Ile
            500                 505                 510
Arg Arg Ala Lys Asn Phe Ile Tyr Ile Glu Asn Gln Tyr Phe Leu Gly
        515                 520                 525
Ser Ser Tyr Ala Trp Lys Pro Glu Gly Ile Lys Pro Glu Asp Ile Gly
530                 535                 540
Ala Leu His Leu Ile Pro Lys Glu Leu Ala Leu Lys Val Val Ser Lys
545                 550                 555                 560
Ile Glu Ala Gly Glu Arg Phe Thr Val Tyr Val Val Val Pro Met Trp
                565                 570                 575
Pro Glu Gly Val Pro Glu Ser Gly Ser Val Gln Ala Ile Leu Asp Trp
            580                 585                 590
Gln Arg Arg Thr Met Glu Met Met Tyr Thr Asp Ile Thr Glu Ala Leu
        595                 600                 605
Gln Ala Lys Gly Ile Glu Ala Asn Pro Lys Asp Tyr Leu Thr Phe Phe
    610                 615                 620
Cys Leu Gly Asn Arg Glu Val Lys Gln Ala Gly Glu Tyr Gln Pro Glu
625                 630                 635                 640
Glu Gln Pro Glu Ala Asp Thr Asp Tyr Ser Arg Ala Gln Glu Ala Arg
                645                 650                 655
Arg Phe Met Ile Tyr Val His Thr Lys Met Met Ile Val Asp Asp Glu
            660                 665                 670
Tyr Ile Ile Ile Gly Ser Ala Asn Ile Asn Gln Arg Ser Met Asp Gly
```

```
                    675                      680                      685
      Ala  Arg  Asp  Ser  Glu  Ile  Ala  Met  Gly  Gly  Tyr  Gln  Pro  Tyr  His  Leu
           690                      695                      700
      Ala  Thr  Arg  Gln  Pro  Ala  Arg  Gly  Gln  Ile  His  Gly  Phe  Arg  Met  Ala
      705                      710                      715                      720
      Leu  Trp  Tyr  Glu  His  Leu  Gly  Met  Leu  Asp  Asp  Val  Phe  Gln  Arg  Pro
                          725                      730                      735
      Glu  Ser  Leu  Glu  Cys  Val  Gln  Lys  Val  Asn  Arg  Ile  Ala  Glu  Lys  Tyr
                     740                      745                      750
      Trp  Asp  Met  Tyr  Ser  Ser  Asp  Asp  Leu  Gln  Gln  Asp  Leu  Pro  Gly  His
                755                      760                      765
      Leu  Leu  Ser  Tyr  Pro  Ile  Gly  Val  Ala  Ser  Asp  Gly  Val  Val  Thr  Glu
           770                      775                      780
      Leu  Pro  Gly  Met  Glu  Tyr  Phe  Pro  Asp  Thr  Arg  Ala  Arg  Val  Leu  Gly
      785                      790                      795                      800
      Ala  Lys  Ser  Asp  Tyr  Met  Pro  Pro  Ile  Leu  Thr  Ser
                          805                      810
```

( 2 ) INFORMATION FOR SEQ ID NO:4:

( i ) SEQUENCE CHARACTERISTICS:
        ( A ) LENGTH: 2799 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: CDS
        ( B ) LOCATION: 1876..1983

( i x ) FEATURE:
        ( A ) NAME/KEY: CDS
        ( B ) LOCATION: 2524..2799

( x i ) SEQUENCE DESCRIPTION: SEQ ID NO:4:

```
CAAGGGTGTA  CATAGATTTG  TCTCGTAAAA  TAGTATTATA  ATATTATAAA  CTTATTACTC      60

TATCCGTTCT  AAAATATAAG  AACCTTATGA  CTGGATGGAA  CATTTCCTAG  TACTACGAAT     120

CTGAACACAT  GTCTAGATTC  ATAGTACTAG  GAAATGTCTC  ATCGCGGTAC  TAGGTTCTTA     180

TATTTTAGGA  TGGAGGGAGT  TTAATATAAA  ACTAATGGTT  AGAACTTTGA  AAGTTTGATT     240

TTAAATGTCA  AATATTTATG  GCTGGAGGTA  GTATAATATG  TTTTTTTTGG  GACGTAGACT     300

AGGTAGTATA  ATATGTTTGG  TTGTGTTTAG  ATCCAATATT  TGGATCCAAA  CTTCAGTCAT     360

TTTCCATCAC  ATCAACTTGT  CATATACACA  TAACTTTTCA  GTCACATCAT  CCCCAATTTC     420

AACCAAAATC  AAACTTTGCG  CTGAACTAAA  CACAACCTTT  GGGCCCGTTT  AGTTCCCCAA     480

TTTTTTTCCC  AAAAACATCA  CATCGAATCT  TTGGACACAT  GCATGAAGCA  TTAAATATAG     540

ATAAAAAGAA  AAACTAATTG  CACAGTTATG  GAGGAAATCG  CGAGACGAAT  CTTTTAAGCC     600

TAATTAGTCC  GTGATTAGCC  ATAAGTGCTA  CAGTAACCCA  ATTGTGCTAA  TGACGGCTTA     660

ATTAGTCTCC  ACAAGATTCG  TCTCGCAGTT  TCCAGGCGAG  TTCTGAAATT  AGTTTTTTCA     720

TTCGTGTCCG  AAAACCCCTT  CCGACATCCG  GTCAAACGTT  CGATATGACA  CCCACAAATT     780

TTCTTTTCCC  CAACTAAACA  CACCCTTTAT  CTCTTACCCT  CTGGCTCTTT  CAGTAGGCAT     840

ATCCAAGACA  GCTGGTAATG  CAGGCTCGGA  CATAATTTGA  CAGTTACGTT  CATGTGACCG     900

ACGGTTGATG  CTAGTGCAAC  TGCAACATAC  TGTTCAGATG  GATGTCCCAA  CGAGCTCAAA     960

ACAACTTAGG  TGGCGCGTCG  CGATTCATCA  ATAACTCAAA  TGGAAGCGCA  AGTGCACGTA    1020
```

-continued

| | | | | | |
|---|---|---|---|---|---|
| CGAAAATGAC | AGCGAGTGAG | GTGGCGAGCC | TCACCTTGGT | GATCCCAACC | GGATAAGCTA | 1080 |
| TGCATCAGCC | AGTTTCGTGG | GGCTGCACAT | TTCGTCGAAC | ACCTGGAGTC | CACGCCGCCG | 1140 |
| GCGACGTCGG | CACAGCGCGC | CCGCCCACCG | CCCACGCACG | CGCTTGACTC | CACCCATGTT | 1200 |
| CTCCCTTCTC | GACGCCCGCG | AAGCCAGCGA | ACCGATCCGA | GGAAGTCAAG | CCCCCACCGC | 1260 |
| CACTTGGACC | GACCTCGGGA | CGACGACGCC | CCGCGCTCT | TCTAGACGCG | CGGACGACGC | 1320 |
| GGGCGCTGGC | TCCGCGACGC | GACGTCGCGG | TCATGGAGTA | ACCGCGACGG | ACAGATACTT | 1380 |
| CTACCCGTTT | TTAACCTCGC | CTCCTCCTCC | TCCCGGCTCG | AGATCCGTGG | CCACGACGCG | 1440 |
| TGGTGGGAAA | CCGGGAACGA | CGTGCACGCA | CGCACACAGG | GCAAGTTTCA | GTAGAAAAAT | 1500 |
| CGCCGGCATC | CAGATCGGGA | CAGTCTCTCT | TCTCCCGCAA | TTTTATAATC | TCGCTCGATC | 1560 |
| CAATCTGCTC | CCCTTCTTCT | TCTACTCTCC | CCATCTCGGC | TCTCGCCATC | GCCATCCTCC | 1620 |
| TCTCCCTTCC | CGGAGAAGAC | GCCTCCCTCC | GCCGATCACC | ACCCGGTAAG | CCCAGTGTGC | 1680 |
| TTAGGCTAAG | CGCACTAGAG | CTTCTTGCTC | GCTTGCTTCT | TCTCCGCTCA | GATCTGCTTG | 1740 |
| CTTGCTTGCT | TCGCTAGAAC | CCTACTCTGT | GCTGCGAGTG | TCGCTGCTTC | GTCTTCCTTC | 1800 |
| CTCAAGTTCG | ATCTGATTGT | GTGTGTGGGG | GGGCGCAGGT | AGGGCGAGGA | GGGAGCCAAA | 1860 |

```
TCCAAATCAG  CAGCC ATG GCG CAG ATG CTG CTC CAT GGG ACG CTG CAC GCC                 1911
            Met Ala Gln Met Leu Leu His Gly Thr Leu His Ala
              1               5                  10

ACC ATC TTC GAG GCG GCG TCG CTC TCC AAC CCG CAC CGC GCC AGC GGA                   1959
Thr Ile Phe Glu Ala Ala Ser Leu Ser Asn Pro His Arg Ala Ser Gly
     15                  20                  25

AGC GCC CCC AAG TTC ATC CGC AAG GTTCGGACCC TTCTCCTTAA TCTACTCGTC                  2013
Ser Ala Pro Lys Phe Ile Arg Lys
     30                  35

TTTGCTCTTG CTCTTTTTCT TTTGTGTCCC TTTCTTGTGT GTGCGTTTGC ATGAGCCCGA                 2073
ATTTGATCTG CTAGTGCACA GTACAGTCAG ATACACTGAA ACGATCTGGA AATTCTGGAT                 2133
TATTAGGAAA AATAAAGAGG TAGTAGACAA GAATTGGAGA TACTTTCTAT CAAGATTGGT                 2193
CTATTATGCT TGGCCATTTC TTGTTTGACC CAAGTACTTC TTTGAATCTA GAGTTTGCTG                 2253
TGTGTGATGT GGTGTGTGTT TGTGTCACCA AAAATCTTCA TTAGCTAAAA CTGAAATTTT                 2313
ATTTATTAAC TGACCTACTA AAAATGTAGA GTTCTCTGTG TGTGATGTGT GCTTGTGTCA                 2373
CCAAAAATCT TGATTTGATA GAGTTTTTAT TTATTTATTA ACTGACCTAC TACAAATCTA                 2433
TTGCTGTATG CTATGTGTGT CTGTATCACC TGAAATGCAA TGTCTTCTTC TTTGTTGTTC                 2493

TTGATCTAAC ACGTGAGCTC ATGTCAACAG TTT GTG GAG GGG ATT GAG GAC ACT                  2547
                                   Phe Val Glu Gly Ile Glu Asp Thr
                                                           40

GTG GGT GTC GGC AAA GGC GCC ACC AAG GTG TAT TCT ACC ATT GAT CTG                   2595
Val Gly Val Gly Lys Gly Ala Thr Lys Val Tyr Ser Thr Ile Asp Leu
 45                  50                  55                  60

GAG AAA GCT CGT GTA GGG CGA ACT AGG ATG ATA ACC AAT GAG CCC ATC                   2643
Glu Lys Ala Arg Val Gly Arg Thr Arg Met Ile Thr Asn Glu Pro Ile
             65                  70                  75

AAC CCT CGC TGG TAT GAG TCG TTC CAC ATC TAT TGC GCT CAT ATG GCT                   2691
Asn Pro Arg Trp Tyr Glu Ser Phe His Ile Tyr Cys Ala His Met Ala
         80                  85                  90

TCC AAT GTG ATC TTC ACT GTC AAG ATT GAT AAC CCT ATT GGG GCA ACG                   2739
Ser Asn Val Ile Phe Thr Val Lys Ile Asp Asn Pro Ile Gly Ala Thr
     95                  100                 105

AAT ATT GGG AGG GCT TAC CTG CCT GTC CAA GAG CTT CTC AAT GGA GAG                   2787
Asn Ile Gly Arg Ala Tyr Leu Pro Val Gln Glu Leu Leu Asn Gly Glu
 110                 115                 120
```

```
        GAG ATT GAC AGA                                                                          2799
        Glu Ile Asp Arg
        125
```

( 2 ) INFORMATION FOR SEQ ID NO:5:

( i ) SEQUENCE CHARACTERISTICS:
        ( A ) LENGTH: 36 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:5:

```
Met Ala Gln Met Leu Leu His Gly Thr Leu His Ala Thr Ile Phe Glu
 1               5                  10                  15

Ala Ala Ser Leu Ser Asn Pro His Arg Ala Ser Gly Ser Ala Pro Lys
            20                  25                  30

Phe Ile Arg Lys
            35
```

( 2 ) INFORMATION FOR SEQ ID NO:6:

( i ) SEQUENCE CHARACTERISTICS:
        ( A ) LENGTH: 92 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:6:

```
Phe Val Glu Gly Ile Glu Asp Thr Val Gly Val Gly Lys Gly Ala Thr
 1               5                  10                  15

Lys Val Tyr Ser Thr Ile Asp Leu Glu Lys Ala Arg Val Gly Arg Thr
            20                  25                  30

Arg Met Ile Thr Asn Glu Pro Ile Asn Pro Arg Trp Tyr Glu Ser Phe
            35                  40                  45

His Ile Tyr Cys Ala His Met Ala Ser Asn Val Ile Phe Thr Val Lys
        50                  55                  60

Ile Asp Asn Pro Ile Gly Ala Thr Asn Ile Gly Arg Ala Tyr Leu Pro
 65                 70                  75                  80

Val Gln Glu Leu Leu Asn Gly Glu Glu Ile Asp Arg
                85                  90
```

( 2 ) INFORMATION FOR SEQ ID NO:7:

( i ) SEQUENCE CHARACTERISTICS:
        ( A ) LENGTH: 173 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:7:

```
GTAAGCCCAG TGTGCTTAGG CTAAGCGCAC TAGAGCTTCT TGCTCGCTTG CTTCTTCTCC      60

GCTCAGATCT GCTTGCTTGC TTGCTTCGCT AGAACCCTAC TCTGTGCTGC GAGTGTCGCT     120

GCTTCGTCTT CCTTCCTCAA GTTCGATCTG ATTGTGTGTG TGGGGGGGCG CAG            173
```

( 2 ) INFORMATION FOR SEQ ID NO:8:

( i ) SEQUENCE CHARACTERISTICS:
        ( A ) LENGTH: 10 amino acids (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:8:

Val Gly Lys Gly Ala Thr Lys Val Tyr Ser
    1               5                   10

(2) INFORMATION FOR SEQ ID NO:9:

(i) SEQUENCE CHARACTERISTICS:
        (A) LENGTH: 23 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:9:

Asn Tyr Phe His Gly Ser Asp Val Asn Xaa Val Leu Xaa Pro Arg Asn Pro
    1               5                   10                  15

Asp Asp Xaa Xaa Xaa Ile
                20

(2) INFORMATION FOR SEQ ID NO:10:

(i) SEQUENCE CHARACTERISTICS:
        (A) LENGTH: 33 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:10:

Thr Xaa Asn Val Gln Leu Phe Arg Ser Ile Asp Gly Gly Ala Ala Phe
    1               5                   10                  15

Gly Phe Pro Asp Thr Pro Glu Glu Ala Ala Lys Xaa Gly Leu Val Ser
                20                  25                  30

Gly (2) INFORMATION FOR SEQ ID NO:11:

(i) SEQUENCE CHARACTERISTICS:
        (A) LENGTH: 40 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:11:

Ile Ala Met Gly Gly Tyr Gln Phe Tyr His Leu Ala Thr Arg Gln Pro
    1               5                   10                  15

Ala Arg Gly Gln Ile His Gly Phe Arg Met Ala Leu Xaa Tyr Glu His
                20                  25                  30

Leu Gly Met Leu Xaa Asp Val Phe
                35                  40

(2) INFORMATION FOR SEQ ID NO:12:

(i) SEQUENCE CHARACTERISTICS:
        (A) LENGTH: 14 base pairs
        (B) TYPE: nucleic acid
        (C) STRANDEDNESS: single (D) TOPOLOGY: linear (ii) MOLECULE TYPE: other nucleic acid
    (A) DESCRIPTION: /desc = "oligonucleotide"

(xi) SEQUENCE DESCRIPTION: SEQ ID NO:12:

AAKTAKTTKC AKGG 14

(2) INFORMATION FOR SEQ ID NO:13:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "oligonucleotide"

(xi) SEQUENCE DESCRIPTION: SEQ ID NO:13:

RTCRTCRTCN GGRTT 15

(2) INFORMATION FOR SEQ ID NO:14:

(i) SEQUENCE CHARACTERISTICS:
    (A) LENGTH: 5 amino acids
    (B) TYPE: amino acid
    (C) STRANDEDNESS: Not Relevant
    (D) TOPOLOGY: linear (ii) MOLECULE TYPE: peptide (xi) SEQUENCE DESCRIPTION: SEQ ID NO:14:

Asn Tyr Phe His Gly
1               5

(2) INFORMATION FOR SEQ ID NO:15:

(i) SEQUENCE CHARACTERISTICS:
    (A) LENGTH: 5 amino acids
    (B) TYPE: amino acid
    (C) STRANDEDNESS: Not Relevant
    (D) TOPOLOGY: linear (ii) MOLECULE TYPE: peptide (xi) SEQUENCE DESCRIPTION: SEQ ID NO:15:

Asn Pro Asp Asp Xaa
1               5

(2) INFORMATION FOR SEQ ID NO:16:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (ii) MOLECULE TYPE: other nucleic acid (ix) FEATURE:
    (A) NAME/KEY: CDS
    (B) LOCATION: 2..31

(xi) SEQUENCE DESCRIPTION: SEQ ID NO:16:

C TCT GAC GTG AAC TGT GTT CTA TGC CCT CGC 31
  Ser Asp Val Asn Cys Val Leu Cys Pro Arg
  1               5                  10

(2) INFORMATION FOR SEQ ID NO:17:

(i) SEQUENCE CHARACTERISTICS:
  (A) LENGTH: 10 amino acids
  (B) TYPE: amino acid
  (D) TOPOLOGY: linear  (ii) MOLECULE TYPE: protein  (xi) SEQUENCE DESCRIPTION: SEQ ID NO:17:

```
Ser  Asp  Val  Asn  Cys  Val  Leu  Cys  Pro  Arg
 1                    5                       10
```

(2) INFORMATION FOR SEQ ID NO:18:

(i) SEQUENCE CHARACTERISTICS:
  (A) LENGTH: 15 base pairs
  (B) TYPE: nucleic acid
  (C) STRANDEDNESS: single
  (D) TOPOLOGY: linear  (ii) MOLECULE TYPE: other nucleic acid
  (A) DESCRIPTION: /desc = "primer"

(xi) SEQUENCE DESCRIPTION: SEQ ID NO:18:

ACCCGGTAAG CCCAG     15

(2) INFORMATION FOR SEQ ID NO:19:

(i) SEQUENCE CHARACTERISTICS:
  (A) LENGTH: 15 base pairs
  (B) TYPE: nucleic acid
  (C) STRANDEDNESS: single
  (D) TOPOLOGY: linear  (ii) MOLECULE TYPE: other nucleic acid
  (A) DESCRIPTION: /desc = "primer"

(xi) SEQUENCE DESCRIPTION: SEQ ID NO:19:

CCCCCGCGTC CATCC     15